US012756014B2

(12) United States Patent
Qian et al.

(10) Patent No.: US 12,756,014 B2
(45) Date of Patent: Oct. 6, 2026

(54) NON-AQUEOUS ELECTROLYTE AND BATTERY

(71) Applicant: SHENZHEN CAPCHEM TECHNOLOGY CO., LTD., Shenzhen City (CN)

(72) Inventors: Yunxian Qian, Shenzhen City (CN); Shiguang Hu, Shenzhen City (CN); Chaowei Cao, Shenzhen City (CN); Pengkai Guo, Shenzhen City (CN); Chi Wang, Shenzhen City (CN); Shuhuai Xiang, Shenzhen City (CN); Qun Chen, Shenzhen City (CN); Yonghong Deng, Shenzhen City (CN)

(73) Assignee: SHENZHEN CAPCHEM TECHNOLOGY CO., LTD., Shenzhen City (CN)

( * ) Notice: Subject to any disclaimer, the term of this patent is extended or adjusted under 35 U.S.C. 154(b) by 615 days.

(21) Appl. No.: 18/258,422

(22) PCT Filed: Dec. 16, 2021

(86) PCT No.: PCT/CN2021/138674

§ 371 (c)(1),
(2) Date: Jun. 20, 2023

(87) PCT Pub. No.: WO2022/143190

PCT Pub. Date: Jul. 7, 2022

(65) Prior Publication Data

US 2024/0055659 A1 Feb. 15, 2024

(30) Foreign Application Priority Data

Dec. 28, 2020 (CN) ......................... 202011606717.2
Apr. 13, 2021 (CN) ......................... 202110392818.2

(51) Int. Cl.

| | |
|---|---|
| ***H01M 10/0567*** | (2010.01) |
| ***C07D 411/14*** | (2006.01) |
| ***H01M 4/131*** | (2010.01) |
| ***H01M 4/525*** | (2010.01) |
| ***H01M 10/0525*** | (2010.01) |
| *H01M 4/02* | (2006.01) |

(52) U.S. Cl.

CPC ....... *H01M 10/0567* (2013.01); *C07D 411/14* (2013.01); *H01M 4/131* (2013.01); *H01M 4/525* (2013.01); *H01M 10/0525* (2013.01); *H01M 2004/028* (2013.01); *H01M 2300/0025* (2013.01)

(58) Field of Classification Search

CPC ......... H01M 10/0525; H01M 10/0566; H01M 10/0567; H01M 10/0568; H01M 10/0569; H01M 2004/028; H01M 2300/0025; H01M 4/131; H01M 4/485; H01M 4/505; H01M 4/525; Y02E 60/10

See application file for complete search history.

(56) References Cited

U.S. PATENT DOCUMENTS

| | | | | |
|---|---|---|---|---|
| 2020/0020972 | A1* | 1/2020 | Shi | H01M 10/0569 |
| 2021/0296703 | A1* | 9/2021 | Sugawara | H01M 10/052 |
| 2024/0136576 | A1* | 4/2024 | Lin | H01M 4/505 |

FOREIGN PATENT DOCUMENTS

| | | | |
|---|---|---|---|
| CN | 107508000 | 12/2017 | |
| CN | 108808066 | 11/2018 | |
| CN | 109119598 | 1/2019 | |
| CN | 109942534 | 6/2019 | |
| CN | 110931863 | 3/2020 | |
| CN | 111755753 | 10/2020 | |
| WO | WO-2020022452 A1 * | 1/2020 | H01M 10/0525 |

OTHER PUBLICATIONS

Machine translation CN109119598A (Year: 2019).*
Machine translation CN111755753A (Year: 2020).*
EPO, Extended European Search Report for EP Application No. 21913931.8, Nov. 5, 2024.
Ota et al., "Structural and Functional Analysis of Surface Film on Li Anode in Vinylene Carbonate-Containing Electrolyte," Journal of the Electrochemical Society, vol. 151, 2004.
CNIPA, First Office Action for CN Application No. 202110392818.2, Aug. 21, 2024.
WIPO, International Search Report for PCT/CN2021/138674, Mar. 17, 2022.

* cited by examiner

*Primary Examiner* — Victoria H Lynch
(74) *Attorney, Agent, or Firm* — Hodgson Russ LLP

(57) ABSTRACT

Provided are a non-aqueous electrolyte comprising a solvent, an electrolyte salt and a first additive, wherein the first additive is selected from at least one of the compounds as shown in structural formula 1: A-D-B-E-C, structural formula 1, wherein A, B, and C are each independently selected from the group consisting of cyclic carbonate groups, cyclic sulfate groups, cyclic sulfite groups, cyclic sulfonate groups, cyclic sulfone groups, cyclic sulfoxide groups, cyclic carboxylate groups or cyclic anhydride groups; D and E are each independently selected from single bond, or groups containing hydrocarbylene groups, ether bonds, sulfur-oxygen double bonds or carbon-oxygen double bonds; and the content of methanol in the non-aqueous electrolyte is 200 ppm or less. Further disclosed is a battery comprising the non-aqueous electrolyte.

12 Claims, No Drawings

NON-AQUEOUS ELECTROLYTE AND BATTERY

CROSS-REFERENCE TO RELATED APPLICATIONS

This application is a U.S. national phase application of International Application No. PCT/CN2021/138674, filed on Dec. 16, 2021, which claims priority to Chinese Patent Application No. 202011606717.2, filed on Dec. 28, 2020, and Chinese Patent Application No. 202110392818.2, filed on Apr. 13, 2021. The entire disclosures of the above-identified applications are incorporated herein by reference.

TECHNICAL FIELD

The disclosure relates to the field of a battery material, and in particular to a non-aqueous electrolyte and a battery.

BACKGROUND

A lithium-ion battery is widely-applied in daily life and production due to its excellent performance. In recent years, with the development of consumer electronics and new energy vehicles, there has been raising a higher demand by people on the performance of the lithium-ion battery, in particular cycling and storage performances under a high temperature need to be further improved. A non-aqueous electrolyte in the lithium-ion battery plays an important role in the battery performance, where an additive in the non-aqueous electrolyte is of a particular importance on the battery performance under the high temperature. During first charging of the lithium-ion battery, reaction occurs at respective surfaces of positive and negative electrodes becoming in contact with the non-aqueous electrolyte, forming a passive film, which not only prevents further decomposition of the electrolyte, but also plays a role in transporting lithium ions. Therefore, the passive film determines the performance of the lithium-ion battery. While the existing additive contributes to enhancing the cycling and storage performances of the battery to a certain extent though, various disadvantages still present such as high impedance of the formed film with a common negative electrode film-forming additive Vinylene Carbonate (VC), and high cost for storage and transportation under a low temperature for a common positive electrode protection additive 1,3,2-Dioxathiolane 2,2-dioxide (DTD).

On the other hand, various substances in the electrolyte interact with each other, thus generating different effects on the battery performance. For example, one same additive improves the battery performance in an electrolyte system, but does not function when used in another electrolyte system. Therefore, it remains to be further developed on how to reduce the influence of variable factors in the electrolyte, so as to provide an electrolyte that consistently enhances the cycling and storage performances under the high temperature of the battery.

SUMMARY

In an aspect, the disclosure provides in embodiments a non-aqueous electrolyte including: a solvent, an electrolytic salt, and a first additive, wherein the first additive is one or more selected from a compound of formula (I):

$$A-D-B-E-C, \text{ wherein} \quad \text{(I)}$$

A, B and C each are independently selected from a group containing a cyclic carbonate group, a cyclic sulfate group, a cyclic sulfite group, a cyclic sulfonate group, a cyclic sulfone group, a cyclic sulfoxide group, a cyclic carboxylate group or a cyclic anhydride group; and D and E each are independently selected from a single bond, or a group containing a hydrocarbylene group, an ether bond, a sulfur-oxygen double bond, or a carbon-oxygen double bond, wherein the non-aqueous electrolyte is of a methanol content of 200 ppm or less.

In some embodiments, A, B and C each independently contain 1 to 5 of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group(s) and the cyclic anhydride group(s); and a total number of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group (s) and the cyclic anhydride group(s) contained in A, B and C is less than or equal to 10.

In some embodiments, A and C each are independently selected from a group of formula (II):

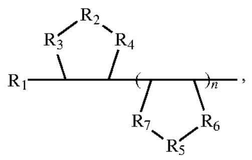

(II)

wherein n is an integer selected from 0 to 4;

$R_1$ is selected from hydrogen, halogen, a $C_1$-$C_5$ hydrocarbyl group or a $C_1$-$C_5$ halogenated hydrocarbyl group;

$R_2$, $R_3$, $R_4$, $R_5$, $R_6$ and $R_7$ each are independently selected from a $C_1$-$C_3$ hydrocarbylene group, a $C_1$-$C_3$ alkoxy group, an oxygen atom,

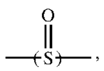, 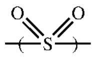 or 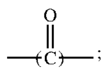;

at least one among $R_2$, $R_3$ and $R_4$ is selected from

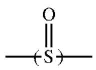, 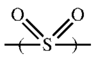 or 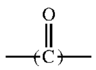, and at least one among $R_2$, $R_3$ and $R_4$ is the oxygen atom; and at least one among $R_5$, $R_6$, and $R_7$ is selected from

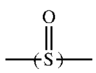, 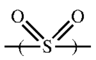 or 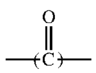, and at least one among $R_5$, $R_6$, and $R_7$ is the oxygen atom.

In some embodiments B is selected from a group of formula (III):

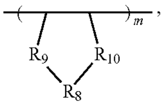

(III)

wherein m is an integer selected from 1 to 4;

$R_8$, $R_9$ and $R_{10}$ each are independently selected from a $C_1$-$C_3$ hydrocarbylene group, a $C_1$-$C_3$ alkoxy group, an oxygen atom,

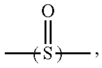, 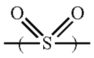 or 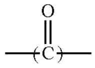;

and at least one among $R_8$, $R_9$ and $R_{10}$ is selected from

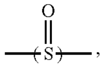, 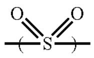 or 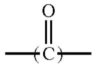, and at least one among $R_8$, $R_9$ and $R_{10}$ is the oxygen atom.

In some embodiments, D and E each are independently selected from a group of formula (IV):

$$-(R_{11}-R_{12}-R_{13})_z-,$$ (IV)

wherein z is an integer selected from 0 to 4;

$R_{11}$ and $R_{13}$ each are independently selected from a single bond or a $C_1$-$C_5$ hydrocarbylene group; and $R_{12}$ is selected from a single bond,

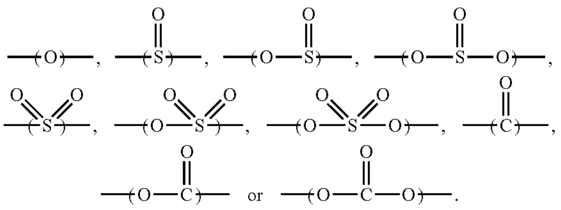

In some embodiments, D and E each are independently selected from a single bond or a $C_1$-$C_5$ hydrocarbylene group; and A, B and C each are independently selected from a substituted or unsubstituted cyclic carbonate group, a substituted or unsubstituted cyclic sulfate group, a substituted or unsubstituted cyclic sulfite group, a substituted or unsubstituted cyclic sulfonate group, a substituted or unsubstituted cyclic sulfone group, a substituted or unsubstituted cyclic sulfoxide group, a substituted or unsubstituted cyclic carboxylate group, or a substituted or unsubstituted cyclic anhydride group.

In some embodiments, when A, B or C is substituted, the substitution is selected from halogen, a hydrocarbyl group, or a halogenated hydrocarbyl group, more preferably, when A, B or C is substituted, the substitution is selected from halogen, an alkyl group or a halogenated alkyl group.

In some embodiments, A and C are same to each other; A and B are same or different to each other; and D and E are same to each other.

In some embodiments, the first additive is one or more selected from the following compounds:

Compound 1-1

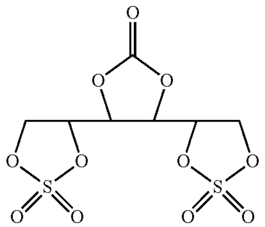

Compound 1-2

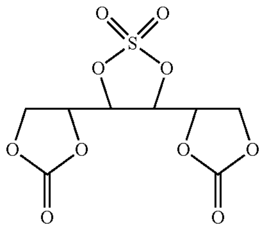

Compound 1-3

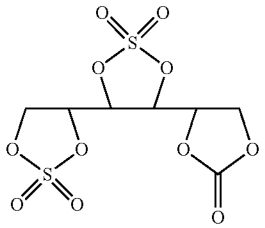

Compound 1-4

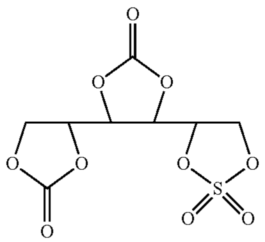

Compound 1-5

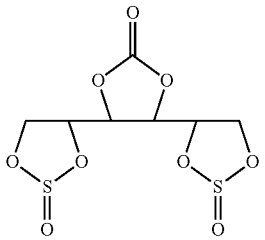

-continued
Compound 1-6
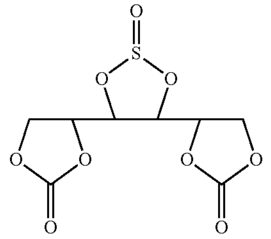
Compound 1-7
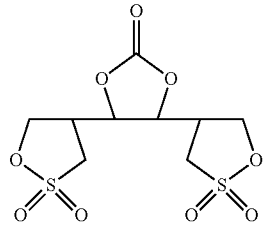
Compound 1-8
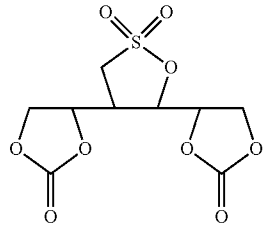
Compound 1-9
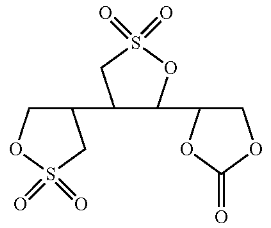
Compound 1-10
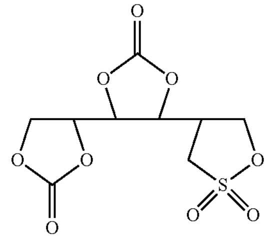
Compound 1-11
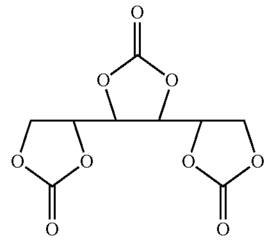
-continued
Compound 1-12
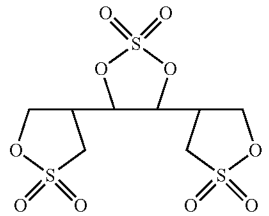
Compound 1-13
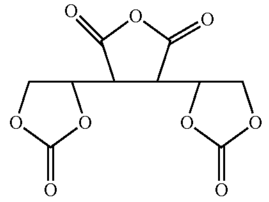
Compound 1-14
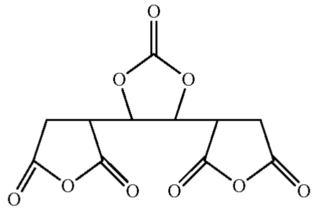
Compound 1-15
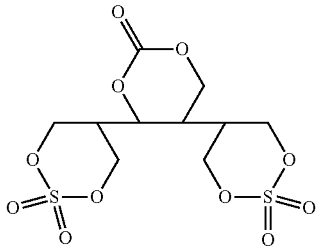
Compound 1-16
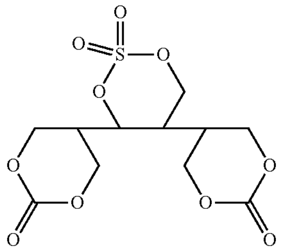
Compound 1-17
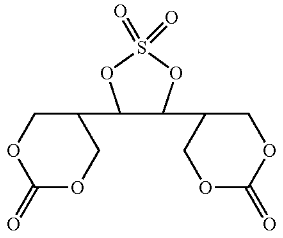

-continued
Compound 1-18
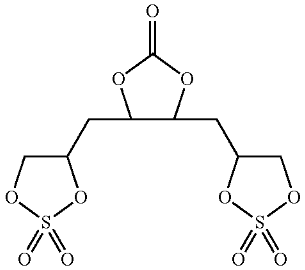
Compound 1-19
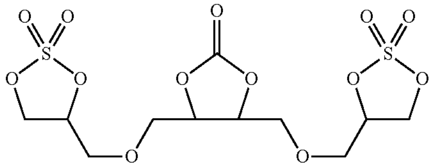
Compound 1-20
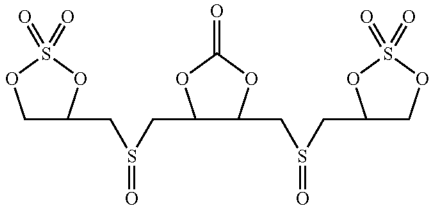
Compound 1-21
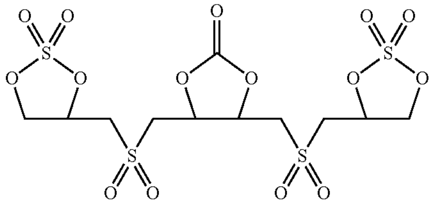
Compound 1-22
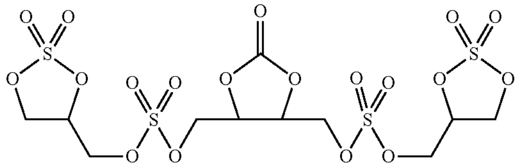
Compound 1-23
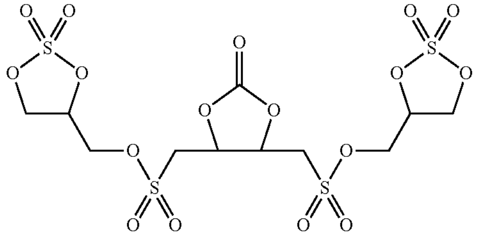
-continued
Compound 1-24
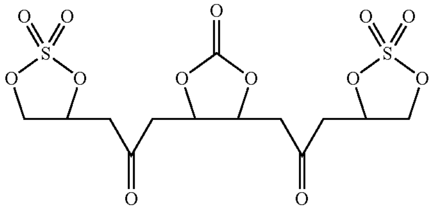
Compound 1-25
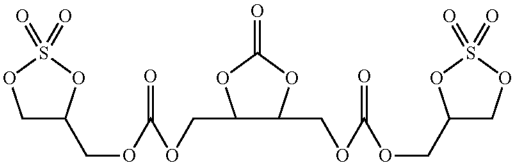
Compound 1-26
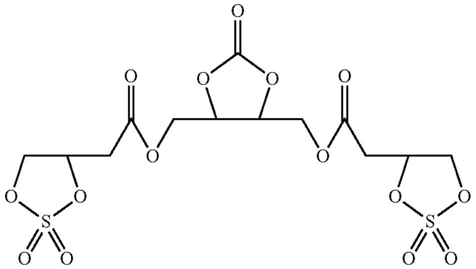
Compound 1-27
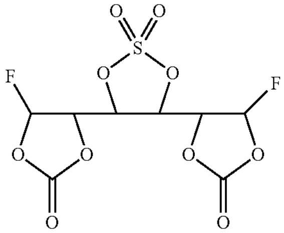
Compound 1-28
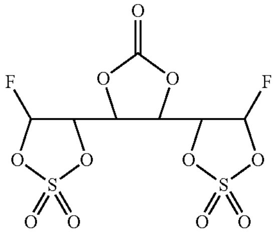
Compound 1-29
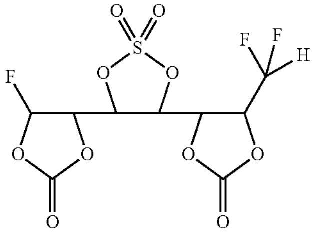

-continued

Compound 1-30

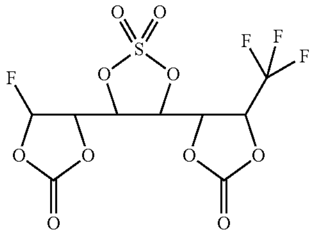

Compound 1-31

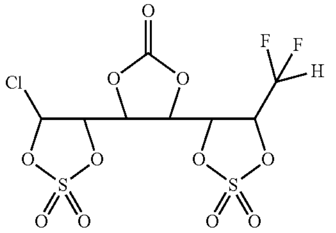

Compound 1-32

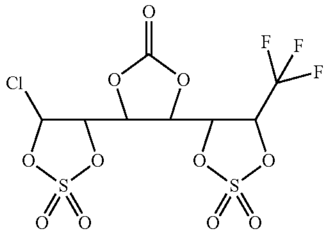

Compound 1-33

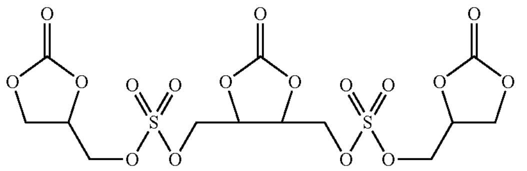

Compound 1-34

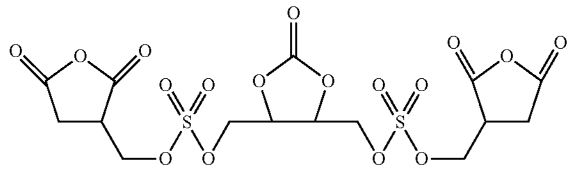

Compound 1-35

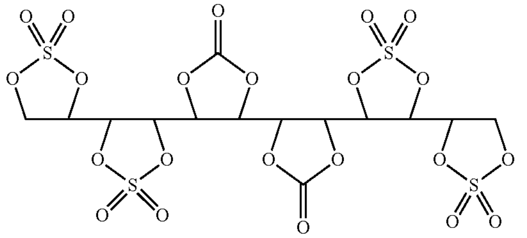

Compound 1-36

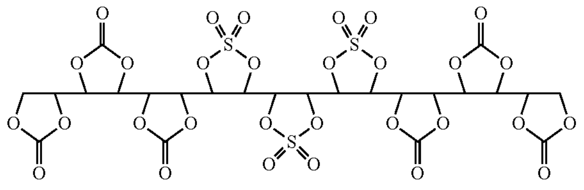

-continued

Compound 1-37

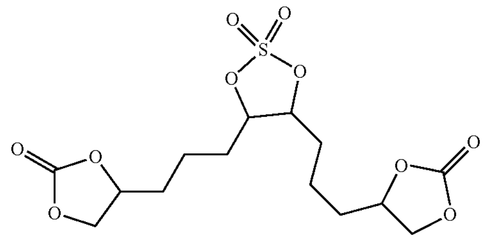

Compound 1-38

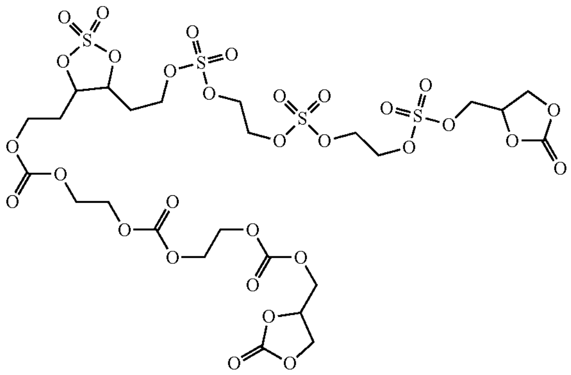

Compound 1-39

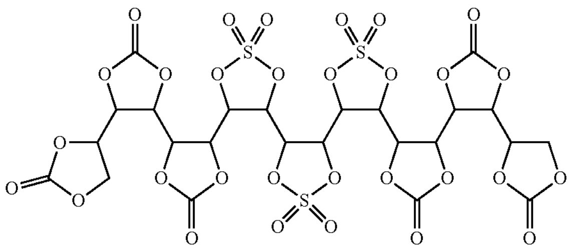

Compound 1-40

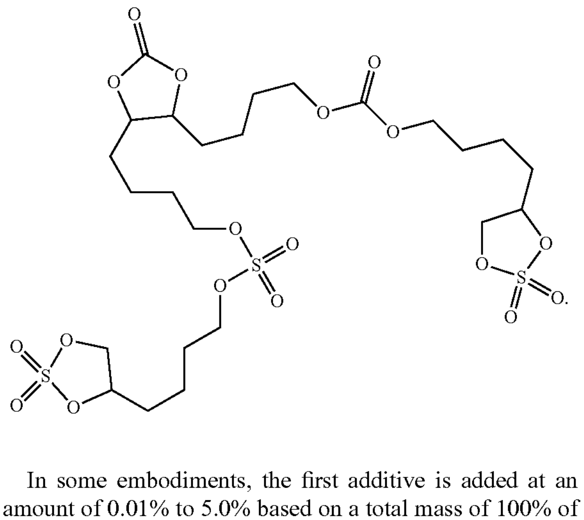

In some embodiments, the first additive is added at an amount of 0.01% to 5.0% based on a total mass of 100% of the non-aqueous electrolyte.

In some embodiments, the non-aqueous electrolyte further includes a second additive; the second additive is one or more selected from a compound of formula (V) and a compound of formula (VI); and the second additive is added at an amount of 0.01% to 4% based on a total mass of 100% of the non-aqueous electrolyte, (V)

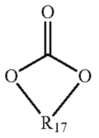

(VI)

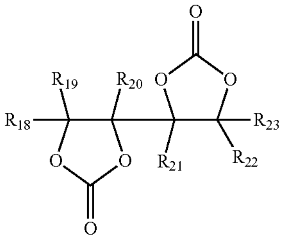

wherein $R_{17}$ is selected from a $C_2$-$C_5$ fluoro-hydrocarbylene group or a $C_2$-$C_5$ unsaturated hydrocarbylene group; and $R_{18}$, $R_{19}$, $R_{20}$, $R_{21}$, $R_{22}$ and $R_{23}$ each are independently selected from a hydrogen atom, a halogen atom, a $C_1$-$C_5$ saturated or unsaturated hydrocarbyl group or a $C_1$-$C_5$ halogenated hydrocarbyl group.

In some embodiments, the compound of formula (V) is one or more selected from the following compounds:

Compound 5-1

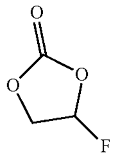

Compound 5-2

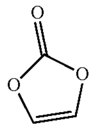

Compound 5-3

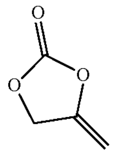

Compound 5-4

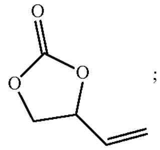

;

and the compound of formula (VI) is one or more selected from the following compounds:

Compound 6-1

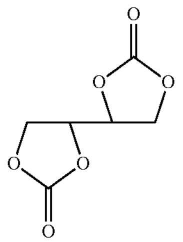

Compound 6-2

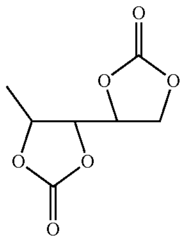

Compound 6-3

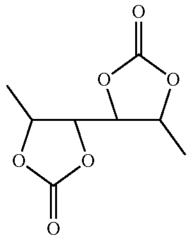

Compound 6-4

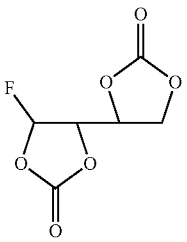

Compound 6-5

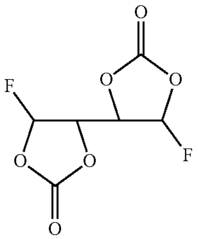

Compound 6-6

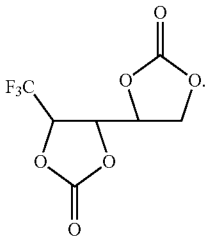

In some embodiments, the non-aqueous electrolyte further includes a third additive; the third additive is one or more selected from $LiPO_2F_2$, LiODFB, LiDFOP, LiBOB, $LiBF_4$, LiFSI and LiTFSI; and the third additive is added at an amount of 0.01% to 4% based on a total mass of 100% of the non-aqueous electrolyte.

In another aspect, the disclosure provides in embodiments a battery including a positive electrode, a negative electrode and the non-aqueous electrolyte as described in any of the above embodiments.

DETAILED DESCRIPTION

In order to make the technical problems, technical solutions and technical effects of the disclosure clearer and more understandable, and the disclosure is further described in details below in conjunction with embodiments. It should be understood that the specific embodiments described herein are intended to explain the disclosure only and are not intended to limit the disclosure.

The disclosure provides in embodiments a non-aqueous electrolyte, including a solvent, an electrolytic salt, and a first additive, wherein the first additive is one or more selected from a compound of formula (I):

$$A{-}D{-}B{-}E{-}C, \text{ wherein} \quad (I)$$

A, B and C each are independently selected from a group containing a cyclic carbonate group, a cyclic sulfate group, a cyclic sulfite group, a cyclic sulfonate group, a cyclic sulfone group, a cyclic sulfoxide group, a cyclic carboxylate group or a cyclic anhydride group; and D and E each are independently selected from a single bond, or a group containing a hydrocarbylene group, an ether bond, a sulfur-oxygen double bond, or a carbon-oxygen double bond, the non-aqueous electrolyte is of a methanol content of 200 ppm or less.

The inventors unexpectedly found through experiments that the compound of formula (I) as the first additive, when added to an electrolyte in some battery systems, significantly enhances the cycling and storage performances under the high temperature of the battery, and reduces gas generation during cycling of the battery; while it is difficult for the compound of formula (I) when added to an alternative electrolyte in other battery systems to achieve improvement. Through experimental backward reasoning, it is found that a certain amount of methanol is detected as an impurity in the electrolyte of those battery systems with insignificantly improved performance; while a less amount of methanol is detected as the impurity in other battery systems with significantly improved performance. Accordingly, it is further verified through experiments with different methanol contents that the improvement of the battery performance by the first additive is related to the methanol content of the electrolyte, where the first additive significantly enhances the cycling and storage performances under the high temperature of the lithium-ion battery when controlling the electrolyte to be of the methanol content of 200 ppm or less.

Regarding a relationship between the first additive and the methanol in the electrolyte, it is speculated that the first additive itself is able to participate in film-forming at the respective surfaces of positive and negative electrodes, but with a quality of the formed film sensitive to methanol, where at a low methanol content, the first additive participates in forming a more stable film, which is less likely to break and reconstitute under the high temperature, while at a methanol content greater than 200 ppm, methanol reacts with the first additive for ester exchange, such that on one hand the first additive undergoes a ring-opening reaction, thus decreasing an effective content of the first additive, and on the other hand a resulting by-product will react with the solvent or the lithium salt in the electrolyte, thereby consuming the electrolyte. Besides, the resulting by-product destroys the film at the surfaces of the positive and negative electrodes.

In some embodiments, A, B and C each independently contain 1 to 5 of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group(s) and the cyclic anhydride group(s); and a total number of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group(s) and the cyclic anhydride group(s) contained in A, B and C is less than or equal to 10.

In some embodiments, A and C each are independently selected from a group of formula (II):

(II)

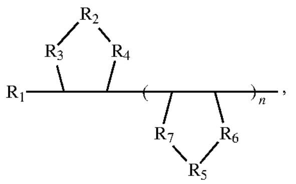

wherein n is an integer selected from 0 to 4;

$R_1$ is selected from hydrogen, halogen, a $C_1$-$C_5$ hydrocarbyl group or a $C_1$-$C_5$ halogenated hydrocarbyl group, $R_2$, $R_3$, $R_4$, $R_5$, $R_6$ and $R_7$ each are independently selected from a $C_1$-$C_3$ hydrocarbylene group, a $C_1$-$C_3$ alkoxy group, an oxygen atom

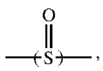, 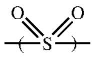 or 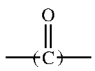;

at least one among $R_2$, $R_3$ and $R_4$ is selected from

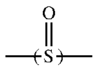, 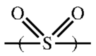 or 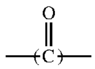, and at least one among $R_2$, $R_3$ and $R_4$ is the oxygen atom; and at least one among $R_5$, $R_6$ and $R_7$ is selected from

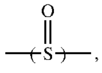, 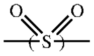 or 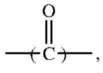, and at least one among $R_5$, $R_6$, and $R_7$ is the oxygen atom.

In preferable embodiments, a combined group of —$R_3$—$R_2$—$R_4$— and a combined group of —$R_7$—$R_5$—$R_6$— each are independently selected from:

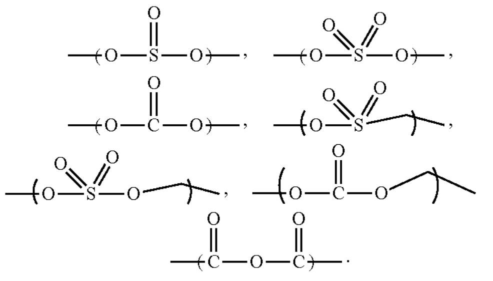

or

In some embodiments, B is selected from a group of formula (III):

(III)

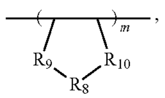

wherein m is an integer selected from 1 to 4;

$R_8$, $R_9$ and $R_{10}$ each are independently selected from a $C_1$-$C_3$ hydrocarbylene group, $C_1$-$C_3$ alkoxy group, an oxygen atom,

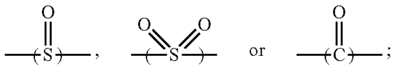

or and at least one among $R_8$, $R_9$ and $R_{10}$ is selected from

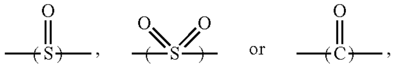

or and at least one among $R_8$, $R_9$ and $R_{10}$ is the oxygen atom.

In preferable embodiments, a combined group of —$R_9$—$R_8$—$R_{10}$— is selected from:

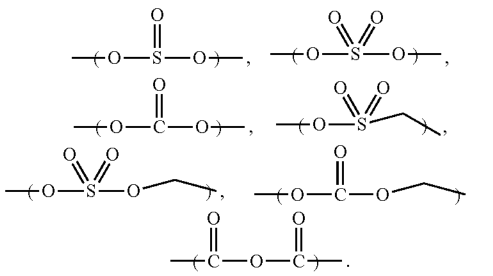

or

In some embodiments, D and E each are independently selected from a group of formula (IV):

$$-(R_{11}-R_{12}-R_{13})_z-, \quad \text{(IV)}$$

wherein z is an integer selected from 0 to 4;

$R_{11}$ and $R_{13}$ each are independently selected from a single bond or a $C_1$-$C_5$ hydrocarbylene group; and $R_{12}$ is selected from a single bond,

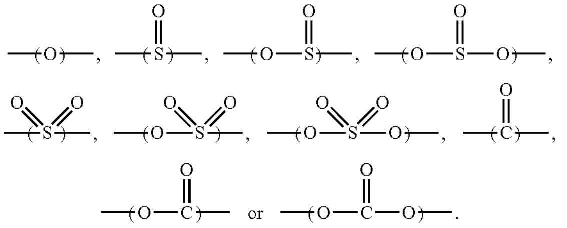

or

In some embodiments, A and C are same to each other; A and B are same or different to each other; and D and E are same to each other.

When A and C are same to each other and D and E are same to each other, the compound of formula (I) is of a symmetrical structure. The compound of formula (I) with the symmetrical structure is easier to synthesize than the asymmetrical one, with a higher yield, thereby contributing to lowering production costs.

In some embodiments, D and E each are independently selected from a single bond or a $C_1$-$C_5$ hydrocarbylene group; and A, B and C each are independently selected from a substituted or unsubstituted cyclic carbonate group, a substituted or unsubstituted cyclic sulfate group, a substituted or unsubstituted cyclic sulfite group, a substituted or unsubstituted cyclic sulfonate group, a substituted or unsubstituted cyclic sulfone group, a substituted or unsubstituted cyclic sulfoxide group, a substituted or unsubstituted cyclic carboxylate group, or a substituted or unsubstituted cyclic anhydride group.

As examples, the first additive is one or more selected from the following compounds:

Compound 1-1

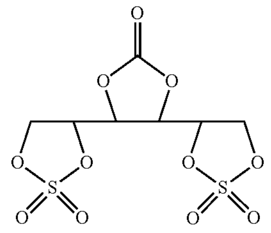

Compound 1-2

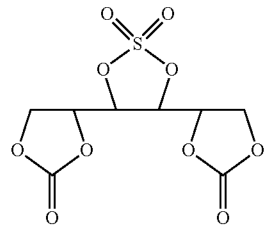

-continued
Compound 1-3
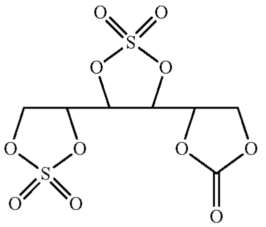
Compound 1-4
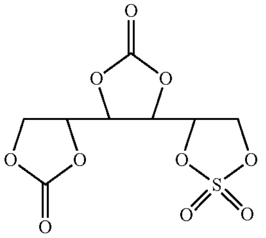
Compound 1-5
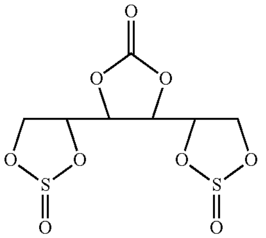
Compound 1-6
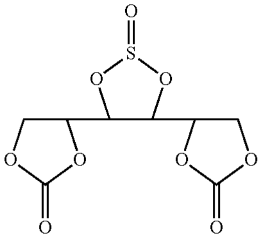
Compound 1-7
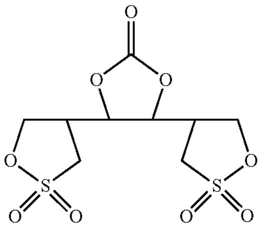
Compound 1-8
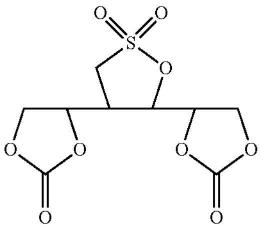
-continued
Compound 1-9
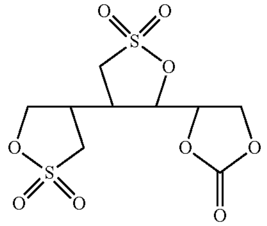
Compound 1-10
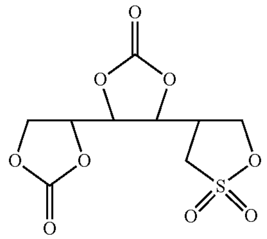
Compound 1-11
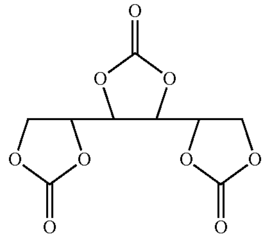
Compound 1-12
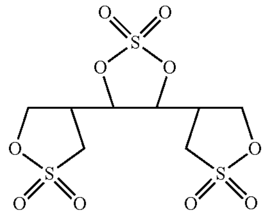
Compound 1-13
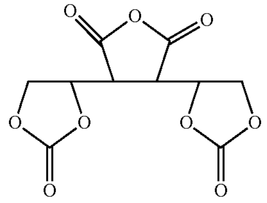
Compound 1-14
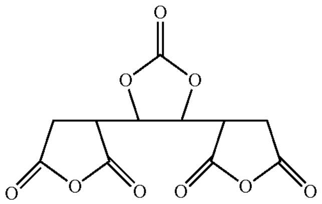
Compound 1-15
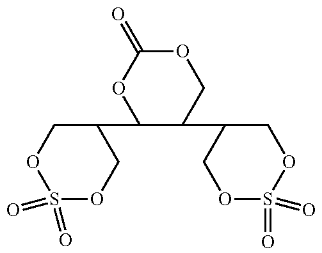

-continued

Compound 1-16

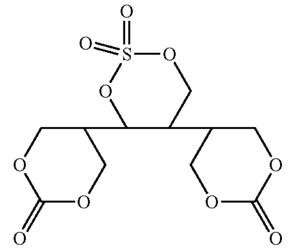

Compound 1-17

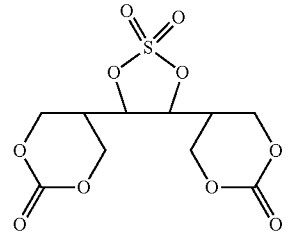

Compound 1-18

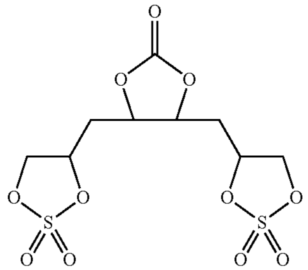

Compound 1-27

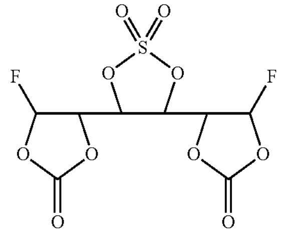

Compound 1-28

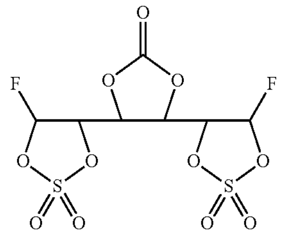

Compound 1-29

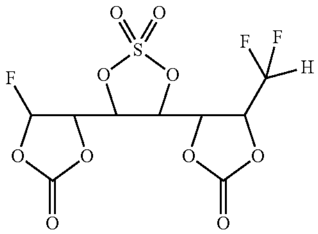

-continued

Compound 1-30

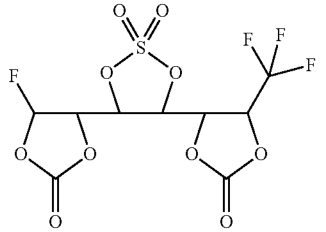

Compound 1-31

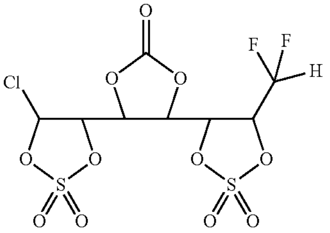

Compound 1-32

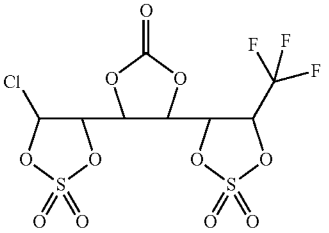

Compound 1-37

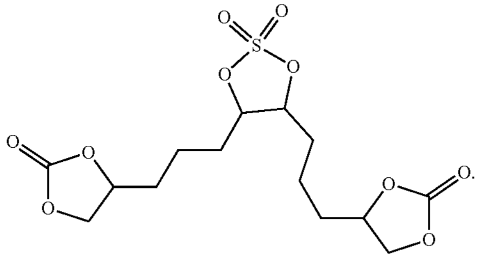

In some embodiments, D and E each are independently selected from a group of formula (IV):

$$-\!\!(R_{11}-R_{12}-R_{13})_z\!\!-, \quad \text{(IV)}$$

wherein z is an integer selected from 1 to 4;

$R_{11}$ and $R_{13}$ each are independently selected from a single bond or a $C_1$-$C_5$ hydrocarbylene group; and $R_{12}$ is selected from a single bond,

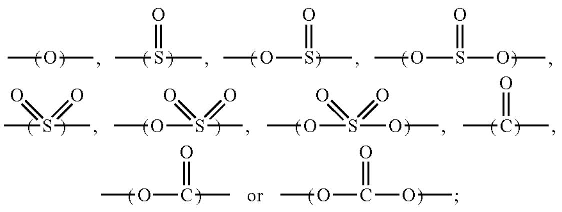

and

A, B and C each are independently selected from a substituted or unsubstituted cyclic carbonate group, a substituted or unsubstituted cyclic sulfate group, a substituted or unsubstituted cyclic sulfite group, a substituted or unsubstituted cyclic sulfonate group, a substituted or unsubstituted cyclic sulfone group, a substituted or unsubstituted cyclic sulfoxide group, a substituted or unsubstituted cyclic carboxylate group, or a substituted or unsubstituted cyclic anhydride group. Preferably, when A, B or C is substituted, the substitution is selected from halogen, a hydrocarbyl group, or a halogenated hydrocarbyl group. More preferably, when A, B or C is substituted, the substitution is selected from halogen, an alkyl group or a halogenated alkyl group.

As examples, the first additive is one or more selected from the following compounds:

Compound 1-19

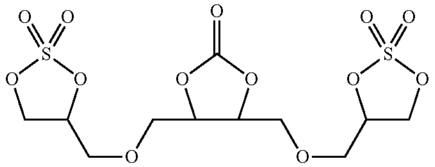

Compound 1-20

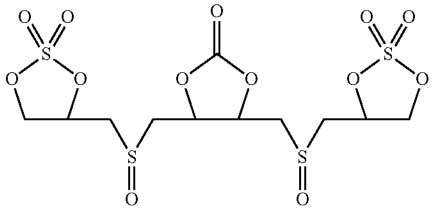

Compound 1-21

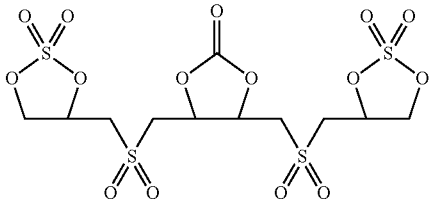

Compound 1-22

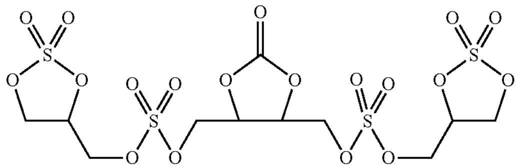

Compound 1-23

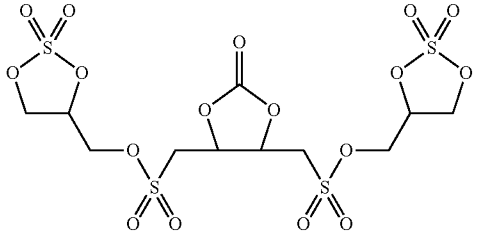

-continued

Compound 1-24

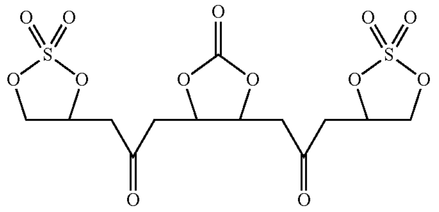

Compound 1-25

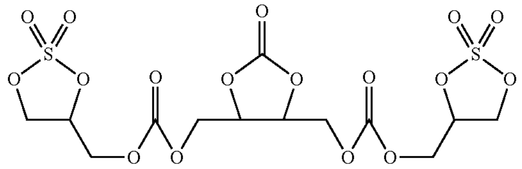

Compound 1-26

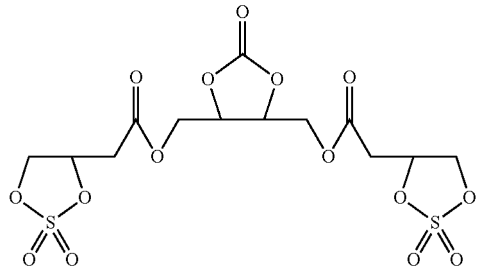

Compound 1-33

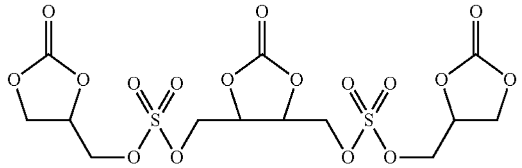

Compound 1-34

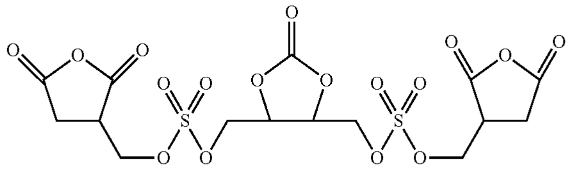

Compound 1-40

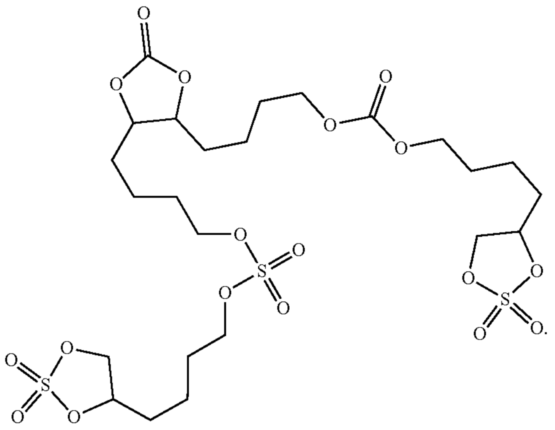

In some embodiments, the first additive may also be one or more selected from the following compounds:

Compound 1-35

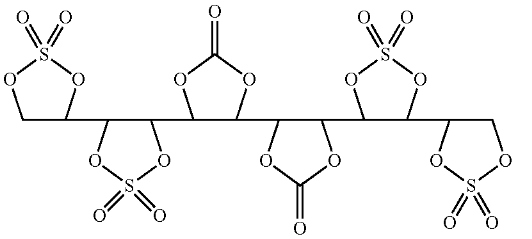

Compound 1-36

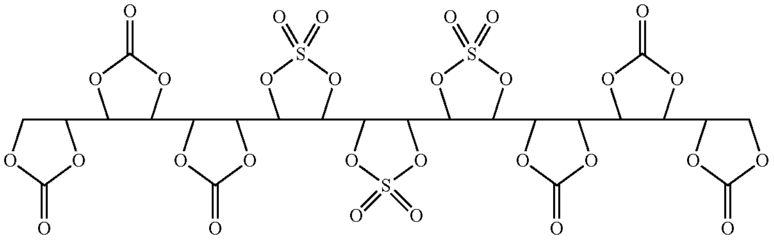

Compound 1-38

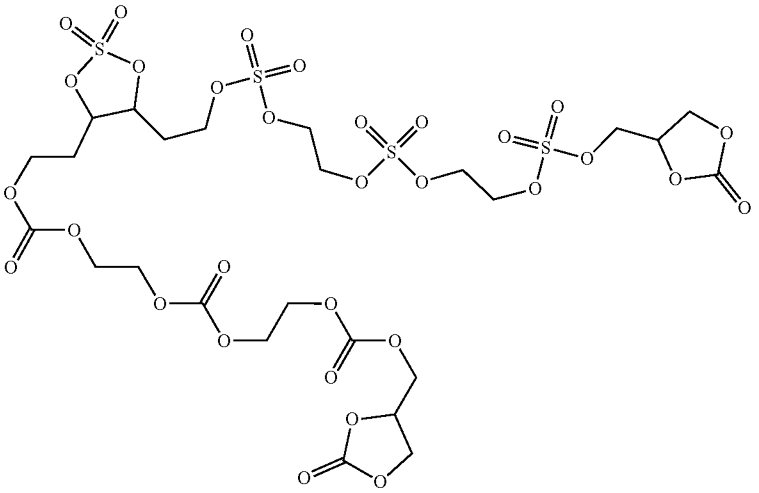

Compound 1-39

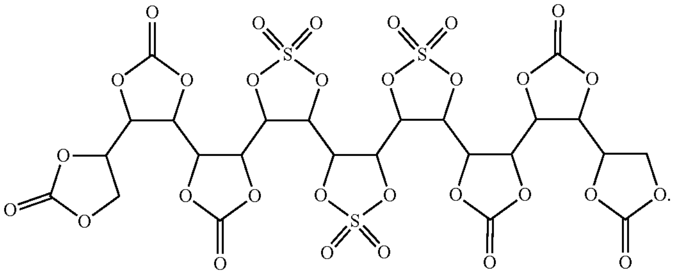

and an organic solvent (such as N,N-Dimethylformamide (DMF)) are added for reaction under heating for several It should be illustrated that the above only illustrates some of the compounds within protection of the disclosure, but are not limited thereto and should not be construed as restrictions on the disclosure.

A person skilled in the art is aware of the preparation method of the above compounds according to common knowledge in the field of chemical synthesis, when a structure of the compound of formula (I) is known.

Compound 1-1 is prepared as below.

To a reaction container, sorbitol, dimethyl carbonate, methanol, an alkaline catalyst (such as potassium hydroxide) hours, followed by adding a certain amount of oxalic acid for pH neutralization, filtering and recrystallizing, thus giving an intermediate product 1. Next, the intermediate product 1, carbonate and dichlorosulfane are subjected to an esterification reaction under a high temperature, thereby obtaining an intermediate product 2, which is then oxidized with an oxidizing agent (such as sodium periodate and like), thus obtaining the compound 1-1.

Compound 1-2 is prepared by as below.

Diacetone-D-mannitol, dimethyl carbonate, methanol, potassium carbonate and dioxane are subjected to reaction under heating and stirring for several hours, followed by adding a certain amount of oxalic acid for pH neutralization, filtering and concentrating, thus giving an intermediate product 3. Next, an appropriate amount of pure water, carbonate and an acid are added to the intermediate product 3 for hydrolysis, thereby obtaining an intermediate product 4. Subsequently, the intermediate product 4, dichlorosulfane, carbonate and a solvent are subjected to reaction under heating, thus giving an intermediate product 5, which is oxidized with the oxidizing agent (such as sodium periodate and like), thus obtaining the compound 1-2.

In some embodiments, the first additive is added at an amount of 0.01% to 5.0% based on a total mass of 100% of the non-aqueous electrolyte.

The first additive, when added at an over-low amount, is not sufficient to form the film for providing protection, thus with insignificantly improved performance of the battery; while the first additive, when added at an over-high amount, not only produces the film with an excessive thickness, thus leading to a high impedance, but also significantly increases a viscosity of the electrolyte, thus adversely affecting the battery performance. Therefore, the electrolyte is added with an appropriate amount of the first additive for improving the battery performance.

In some embodiments, the non-aqueous electrolyte is of a methanol content of 200 ppm or less.

Specifically, the non-aqueous electrolyte is of the methanol content of 0 ppm, 0.1 ppm, 1 ppm, 5 ppm, 10 ppm, 20 ppm, 50 ppm, 100 ppm, 150 ppm or 200 ppm.

It should be noted that the methanol existing in the non-aqueous electrolyte causes deterioration in film-forming by the first additive. Therefore, the non-aqueous electrolyte should be of the methanol content as low as possible within a certain range. The battery with excellent cycling and storage performances under the high temperature is obtainable when the non-aqueous electrolyte is of the methanol content of 200 ppm or less, while further reduction of the methanol content would not results in the significant effect on the film-forming by the first additive.

In some embodiments, the non-aqueous electrolyte further includes a second additive; the second additive is a compound of formula (V) and/or a compound of formula (VI); and the second additive is added at an amount of 0.01% to 4% based on a total mass of 100% of the non-aqueous electrolyte, (V)

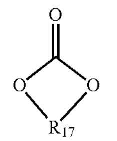

(VI)

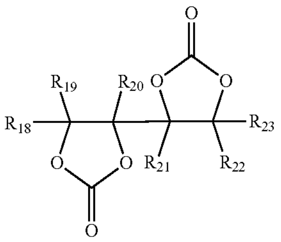

wherein $R_{17}$ is selected from a $C_2$-$C_5$ fluoro-hydrocarbylene group or a $C_2$-$C_5$ unsaturated hydrocarbylene group; and $R_{18}$, $R_{19}$, $R_{20}$, $R_{21}$, $R_{22}$ and $R_{23}$ each are independently selected from a hydrogen atom, a halogen atom, a $C_1$-$C_5$ saturated or unsaturated hydrocarbyl group or a $C_1$-$C_5$ halogenated hydrocarbyl group.

The second additive synergizes with the first additive to form a more stable Solid Electrolyte Interphase (SEI) film at the surface of the negative electrode, thus suppressing gas generation, thereby further enhancing the storage performance under the high temperature.

In some embodiments, the compound of formula (V) is one or more selected from the following compounds:

Compound 5-1

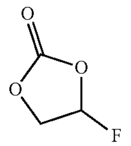

Compound 5-2

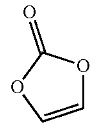

Compound 5-3

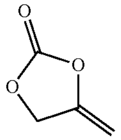

Compound 5-4

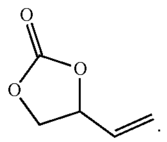

In some embodiments, the compound of formula (VI) is one or more selected from the following compounds:

Compound 6-1

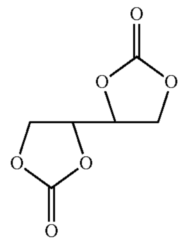

Compound 6-2

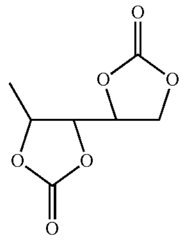

-continued

Compound 6-3

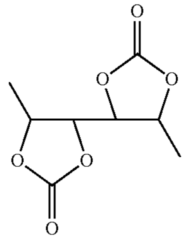

Compound 6-4

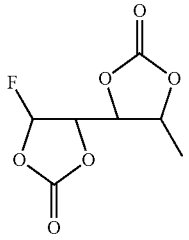

Compound 6-5

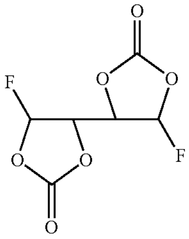

Compound 6-6

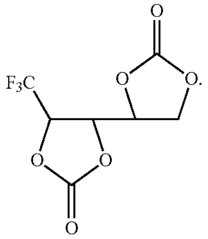

In preferable embodiments, the second additive is added at an amount of 0.01% to 4% based on a total mass of 100% of the non-aqueous electrolyte.

In some embodiments, the first additive and the second additive are added at a total amount of 0.04% to 8% based on a total mass of 100% of the non-aqueous electrolyte.

The first additive and the second additive, when added at the total amount less than 0.04%, are not sufficient to form an entire passive film at the positive and negative electrodes, resulting in decomposition of the electrolyte, with a battery capacity retention rate decayed rapidly after storage under the high temperature due to an unstable decomposition product, and also resulting in severe gas generation that leads to battery expansion. The first additive and the second additive, when added at the total amount greater than 8%, will produce the passive film with an excessive thickness at the positive and negative electrodes, which is detrimental to reducing the impedance of the battery.

In preferable embodiments, the first additive and the second additive are added at the total amount of 1% to 4% based on a total mass of 100% of the non-aqueous electrolyte.

In some embodiments, the non-aqueous electrolyte further includes a third additive; the third additive is one or more selected from $LiPO_2F_2$, LiODFB, LiDFOP, LiBOB, $LiBF_4$, LiFSI and LiTFSI; and the third additive is added at an amount of 0.01% to 4% based on a total mass of 100% of the non-aqueous electrolyte.

The third additive also participates in forming the passive film at the respective surfaces of the positive and negative electrodes. The passive film isolates the electrolyte from direct contact with positive and negative electrode active materials, and reduces a side reaction at an interface from occurring, thereby suppressing the gas generation and inhibiting the impedance from increasing. However, the third additive when added alone results in the passive film formed at the positive and negative electrodes containing more LiF, bringing a difficulty in suppressing LiF from increasing, thus leading to a reduced lithium conductive performance of the passive film with a decreased rate of transporting a lithium ion. Besides, the third additive when added alone results in increased polarization during charging and discharging of the battery, thus leading to a decayed capacity of the battery during storage and cycling under the high temperature, and causing an increasing impedance. The first additive and the third additive when added in combination both participate in film-forming, together constituting components of the film formed at the respective surfaces of the positive and negative electrodes, enhancing dissolution of an inorganic component (LiF, $Li_2CO_3$ and the like) among the components of the film, thus suppressing the inorganic component from generating and increasing, and thereby greatly improving a proportion between an organic component and an inorganic component in the passive film, such that a conductive rate of the lithium ion in the passive film is increased, and the positive and negative electrodes are well protected for improving the battery stability, where the material of the battery is better isolated from contact with the electrolyte, thus reducing the polarization of the battery, suppressing the impedance of the battery cycling under the high temperature from increasing, and improving the cycling performance under the high temperature.

In some embodiments, the solvent includes one or more of an ether solvent, a nitrile solvent, a carbonate solvent and a carboxylate solvent.

In some embodiments, the ether solvent includes cyclic ether or chain ether; the cyclic ether may specifically be, but not limited to, one or more of 1,3-dioxolane (DOL), 1,4-dioxane (DX), crown ether, tetrahydrofuran (THF), 2-methyltetrahydrofuran (2-$CH_3$-THF) and 2-trifluoromethyl tetrahydrofuran (2-$CF_3$-THF); and the chain ether may specifically be, but not limited to, one or more of dimethoxymethane (DMM), 1,2-dimethoxyethane (DME) and diglyme. The nitrile solvent may specifically be, but is not limited, one or more of acetonitrile, glutaronitrile and malononitrile. The carbonate solvent includes cyclic carbonate and chain carbonate; the cyclic carbonate may specifically be, but not limited to, one or more of ethylene carbonate (EC), propylene carbonate (PC), gamma-butyrolactone (GBL) and butylene carbonate (BC); and the chain carbonate may specifically be, but not limited to, one or more of dimethyl carbonate (DMC), methyl ethyl carbonate (EMC), diethyl carbonate (DEC) and dipropyl carbonate (DPC). The carboxylate solvent may specifically be, but not limited to, one or more of methyl acetate (MA), ethyl acetate (EA), propyl acetate (EP), butyl acetate, propyl propionate (PP) and butyl propionate.

In some embodiments, the electrolytic salt includes one or more of a lithium salt, a sodium salt, a potassium salt, a magnesium salt, a zinc salt and an aluminum salt. In preferable embodiments, the electrolytic salt is selected from the lithium salt.

In more preferable embodiments, the electrolytic salt includes one or more of lithium hexafluorophosphate, lithium bis(trifluoromethanesulfonyl)imide and lithium bis (fluorosulfonyl)imide.

In some embodiments, the non-aqueous electrolyte is of an electrolytic salt content of 0.1 mol/L to 8 mol/L. In preferable embodiments, the non-aqueous electrolyte is of the telectrolytic salt content of 0.5 mol/L to 4 mol/L. Specifically, the non-aqueous electrolyte is of the electrolytic salt content of 0.5 mol/L, 1 mol/L, 1.5 mol/L, 2 mol/L, 2.5 mol/L, 3 mol/L, 3.5 mol/L or 4 mol/L.

The disclosure provides in other embodiments a battery, including a positive electrode, a negative electrode and the non-aqueous electrolyte as described in any of the above embodiments.

As the battery includes the non-aqueous electrolyte, the passive film with excellent performance is formed at the positive and negative electrodes, thereby effectively enhancing the cycling and storage performances under the high temperature, thus improving a power performance of the battery.

In some embodiments, the battery is a secondary battery; and the secondary battery may be a lithium secondary battery, a potassium secondary battery, a sodium secondary battery, a magnesium secondary battery, a zinc secondary battery or an aluminium secondary battery and like.

In preferable embodiments, the battery is a lithium metal battery, a lithium ion battery or a lithium-sulfur battery.

In some embodiments, the positive electrode includes a positive electrode active material, the type of which is not particularly limited, as long as it is capable of reversibly embedding/de-embedding a metal ion (such as a lithium ion, a sodium ion, a potassium ion, a magnesium ion, a zinc ion, an aluminum ion and like). Preferably, the positive electrode active material is one or more selected from a nickel-cobalt-manganese ternary material, $LiFePO_4$, $LiCoO_2$ and sulphur and a complex thereof.

In some embodiments, the negative electrode includes a negative electrode active material; and the negative electrode active material includes one or more of a carbon based negative electrode active material, a tin based negative electrode active material, a lithium negative electrode active material, a sodium negative electrode active material, a potassium negative electrode active material, a magnesium negative electrode active material, a zinc negative electrode active material and an aluminum negative electrode active material. The carbon based negative electrode active material may include graphite, hard carbon, soft carbon, graphene, intermediate phase carbon microspheres and like. The tin based negative electrode active material may include tin, tin-carbon, tin-oxygen and a tin-metal compound. The lithium negative electrode active material may include metal lithium or a lithium alloy. The lithium alloy may be specifically at least one of a lithium silicon alloy, a lithium sodium alloy, a lithium potassium alloy, a lithium aluminum alloy, a lithium tin alloy and a lithium indium alloy.

In some embodiments, the battery further includes a diaphragm; and the diaphragm is located between the positive electrode and the negative electrode.

The diaphragm may be an existing conventional diaphragm, such as a polymer diaphragm, a non-woven fabric diaphragm and like, including but not limited to a single layer polypropylene (PP) diaphragm, a single layer polyethylene (PE) diaphragm, a double-layered PP/PE diaphragm, a double-layered PP/PP diaphragm and a triple-layered PP/PE/PP diaphragm and like.

The disclosure is further illustrated in the Examples below. 1. Preparation of batteries in Examples 1 to 59 and Comparative Examples 1 to 16

(1) Preparation of Electrolytes

Ethylene carbonate (EC), diethyl carbonate (DEC) and methyl ethyl carbonate (EMC) were mixed at a mass ratio of EC:DEC:EMC=1:1:1, and lithium hexafluorophosphate ($LiPF_6$) was then added to a molar concentration of 1 mol/L. Subsequently, individual additives were added according to Tables 1 to 5. The amount of the additive was calculated as a percentage of the total mass of the electrolyte. The electrolytes were assayed for the methanol content, which are shown in Tables 1 to 5.

(2) Preparation of a Positive Electrode Plate

A positive electrode active material of $LiNi_{0.5}Co_{0.2}Mn_{0.3}O_2$, a conductive carbon black (Super-P), and a binder of polyvinylidene difluoride (PVDF) were mixed at a mass ratio of 93:4:3, before dispersed in the N-methyl-2-pyrrolidone (NMP), thereby obtaining a positive electrode slurry. The positive electrode slurry was evenly coated on both sides of an aluminum foil, followed by oven drying, calendaring, and vacuum drying. Subsequently, the positive electrode plate was obtained after welding an aluminum lead wire on the aluminum foil with an ultrasonic welder. The positive electrode plate is of a thickness of 120 to 150 μm.

(3) Preparation of a Negative Electrode Plate

A negative electrode active material of graphite, a conductive carbon black (Super-P), and binders of styrene butadiene rubber (SBR) and carboxymethyl cellulose (CMC) were mixed at a mass ratio of 94:1:2.5:2.5, before dispersed in deionized water, thereby obtaining a negative electrode slurry. The negative electrode slurry was evenly coated on both sides of a copper foil, followed by oven drying, calendering and vacuum drying. Subsequently, the negative electrode plate was obtained after welding a nickel lead wire on the copper foil with an ultrasonic welder. The negative electrode plate is of a thickness of 120 to 150 μm.

(4) Preparation of an Electrical Core

A triple-layered diaphragm with a thickness of 20 μm was provided between the positive electrode plate and the negative electrode plate. The sandwich structure composed of the positive electrode plate, the negative electrode plate and the diaphragm was wound. The winding body was flattened before packed by an aluminum foil bag. After vacuum baking at 75° C. for 48 h, the electrical core to be filled with the electrolyte was obtained.

(5) Filling the Electrode into the Electrical Core and Battery Formation

In a glove box with a water content of 20 ppm or less and an oxygen content of 50 ppm or less, the electrolyte prepared as above was filled into the electrical core, followed by encapsulation under vacuum and still placing at 45° C. for 24 h.

Next, the battery formation was carried out by first charging as the following steps:

charging at a constant current of 0.05 C for 180 min;
charging at a constant current of 0.1 C for 180 min;
charging at a constant current of 0.2 C for 120 min;
ageing at 45° C. for 48 h;
secondary encapsulating under vacuum;
charging at a constant current of 0.2 C to achieve 4.2 V; and
discharging at a constant current of 0.2 C back to 3.0 V.

2. Performance Test 2.1. The lithium-ion batteries prepared in Examples 1 to 48 and Comparative Examples 1 to 9 were tested for the following performances.

Testing on the Cycling Performance Under the High Temperature

In an oven at a constant temperature of 45° C., the lithium-ion battery prepared ($LiNi_{0.5}Co_{0.2}Mn_{0.3}O_2$/AG) was charged at a constant current of 1 C to achieve 4.4 V; then subjected to constant current and constant voltage charging until the current drops to 0.05 C; and then discharged at a constant current of 1 C back to 3.0 V, so as to circulate in this way, and the first discharge capacity and the last discharge capacity were recorded.

The capacity retention rate for cycling under the high temperature was calculated according to the following equation:

Capacity retention rate = last discharge capacity/first discharge capacity × 100%.

Testing on the Storage Performance Under the High Temperature

After the battery formation, the lithium-ion battery ($LiNi_{0.5}Co_{0.2}Mn_{0.3}O_2$/AG) was charged to 4.4 V at a constant current of 1 C at room temperature; then subjected to constant current and constant voltage charging until the current drops to 0.05 C; and then discharged at a constant current of 1 C back to 3.0 V, with an initial discharging capacity and an initial battery volume measured. Subsequently, the lithium-ion battery was charged to a full capacity and stored at 60° C. for 30 days, and then discharged at a constant current of 1 C back to 3.0 V, with a retention capacity and a recovery capacity measured, as well as a latter battery volume after storage under the high temperature. The calculation equations are as follows:

Battery capacity retention rate (%) = retention capacity/initial discharging capacity × 100%;

Battery capacity recovery rate (%) = recovery capacity/initial discharging capacity × 100%;

Volume expansion rate (%) = (latter battery volume after storage − initial battery volume) × 100%.

All conditions in the tests are identical for respective batteries as below, except for the differences listed in the respective tables.

2.1.1 Results from testing the batteries prepared in Examples 1 to 12 and Comparative Examples 1 to 4 are shown in Table 1.

TABLE 1

| Example | Alcohol content (ppm) | The first additive and its content (%) | Capacity retention rate (%) after 1000 cycles under 45° C. at 1 C | Storage at 60° C. for 30 days: Capacity retention rate (%) | Capacity recovery rate % | Volume expansion rate (%) |
|---|---|---|---|---|---|---|
| Example 1 | Methanol: 50 | Compound 1-1: 0.01 | 68.8 | 65.2 | 72.5 | 16.3 |
| Example 2 | Methanol: 50 | Compound 1-1: 0.05 | 70.2 | 67.0 | 73.4 | 16.1 |
| Example 3 | Methanol: 50 | Compound 1-1: 0.5 | 73.4 | 73.3 | 80.6 | 16.2 |
| Example 4 | Methanol: 50 | Compound 1-1: 1 | 77.2 | 80.5 | 87.9 | 10.1 |
| Example 5 | Methanol: 50 | Compound 1-1: 2 | 75.2 | 76.4 | 83.9 | 14.2 |
| Example 6 | Methanol: 50 | Compound 1-1: 3 | 73.2 | 78.4 | 81.8 | 13.7 |
| Example 7 | Methanol: 50 | Compound 1-1: 5 | 76.4 | 78.5 | 84.8 | 13.1 |
| Example 8 | Methanol: 50 | Compound 1-1: 6 | 65.6 | 65.3 | 71.2 | 30.0 |
| Example 9 | Methanol: 80 | Compound 1-1: 1 | 77.0 | 79.8 | 86.5 | 12.0 |
| Example 10 | Methanol: 100 | Compound 1-1: 1 | 76.5 | 79.0 | 86.0 | 13.1 |
| Example 11 | Methanol: 150 | Compound 1-1: 1 | 75.9 | 78.6 | 85.5 | 13.5 |
| Example 12 | Methanol: 200 | Compound 1-1: 1 | 75.1 | 77.7 | 84.3 | 25.2 |
| Comparative Example 1 | Methanol: 50 | — | 63.4 | 63.3 | 69.9 | 27.3 |
| Comparative Example 2 | Methanol: 250 | Compound 1-1: 1 | 67.2 | 66.5 | 70.9 | 30.1 |
| Comparative Example 3 | Methanol: 300 | Compound 1-1: 1 | 62.2 | 65.4 | 67.8 | 36.1 |
| Comparative Example 4 | Methanol: 500 | Compound 1-1: 1 | 57.2 | 60.5 | 64.9 | 39.1 |
| Comparative Example 5 | Methanol: 300 | — | 50.4 | 53.3 | 59.9 | 45.3 |

As can be seen from the testing results in Table 1, when the electrolyte is of a methanol content of 200 ppm or less, the compounds of formula (I) as the first additive well enhances the cycling and storage performances under the high temperature of the battery, with the adding amount of the first additive varied within a large range. Furthermore, the cycling and storage performances under the high temperature of the battery are enhanced before decreased as the adding amount of the first additive increases. In particular, when the adding amount of the first additive is 1%, the battery exhibits an optimal overall performance.

When the electrolyte is of a methanol content higher than 200 ppm, the battery is not improved for the performance even the first additive is added in the optimal ratio, indicating that an unfavorable side reaction occurs between methanol and the first additive, thus preventing the battery performance from improvement.

2.1.2 Results from testing the batteries prepared in Examples 12 to 18 and Comparative Examples 2 and 6 are shown in Table 2.

TABLE 2

| Example | Alcohol content | The first additive and its content (%) | Capacity retention rate (%) after 1000 cycles under 45° C. at 1 C | Storage at 60° C. for 30 days | | |
|---|---|---|---|---|---|---|
| | | | | Capacity retention rate (%) | Capacity recovery rate (%) | Volume expansion rate (%) |
| Example 12 | Methanol: 200 | Compound 1-1: 1 | 75.1 | 77.7 | 84.3 | 25.2 |
| Example 13 | Ethanol: 200 | Compound 1-1: 1 | 76.5 | 81.0 | 89.0 | 9.1 |
| Example 14 | Ethylene glycol: 200 | Compound 1-1: 1 | 77.0 | 79.3 | 86.6 | 12.1 |
| Example 15 | Methanol: 50<br>Ethylene glycol: 150 | Compound 1-1: 1 | 78.0 | 80.7 | 88.1 | 9.6 |
| Example 16 | Ethanol: 250 | Compound 1-1: 1 | 76.2 | 80.5 | 87.8 | 13.5 |
| Example 17 | Ethylene glycol: 250 | Compound 1-1: 1 | 76.0 | 78.3 | 84.5 | 16.7 |
| Example 18 | Methanol: 50<br>Ethylene glycol: 200 | Compound 1-1: 1 | 76.3 | 78.2 | 85.4 | 14.6 |
| Comparative Example 2 | Methanol:250 | Compound 1-1: 1 | 67.2 | 66.5 | 70.9 | 30.1 |
| Comparative Example 6 | Methanol: 220<br>Ethylene glycol: 30 | Compound 1-1: 1 | 67.9 | 67.0 | 71.3 | 28.5 |

As can be seen from the testing results in Table 2, methanol induces the most obvious deterioration against the first additive as compared to other alcohols such as ethanol and ethylene glycol, indicating certain specificity for the reaction between methanol and the first additive.

2.1.3 Results from testing the batteries prepared in Examples 19 to 36 and Comparative Example 1 are shown in Table 3.

TABLE 3

| Example | Alcohol content (ppm) | The first additive and its content (%) | Capacity retention rate (%) after 1000 cycles under 45° C. at 1 C | Storage at 60° C. for 30 days | | |
|---|---|---|---|---|---|---|
| | | | | Capacity retention rate (%) | Capacity recovery rate (%) | Volume expansion rate (%) |
| Example 19 | Methanol: 50 | Compound 1-2: 1 | 81.3 | 88.5 | 93.9 | 8.5 |
| Example 20 | Methanol: 50 | Compound 1-4: 1 | 76.2 | 77.6 | 80.6 | 10.2 |
| Example 21 | Methanol: 50 | Compound 1-8: 1 | 78.1 | 81.1 | 85.4 | 11.4 |
| Example 22 | Methanol: 50 | Compound 1-11: 1 | 77.6 | 78.3 | 81.0 | 12.0 |
| Example 23 | Methanol: 50 | Compound 1-14: 1 | 75.4 | 82.3 | 84.9 | 13.9 |
| Example 24 | Methanol: 50 | Compound 1-15: 1 | 76.3 | 82.3 | 86.0 | 12.9 |
| Example 25 | Methanol: 50 | Compound 1-18: 1 | 77.3 | 82.2 | 85.5 | 12.8 |
| Example 26 | Methanol: 50 | Compound 1-19: 1 | 76.9 | 81.9 | 86.5 | 12.1 |
| Example 27 | Methanol: 50 | Compound 1-22: 1 | 76.8 | 82.7 | 85.7 | 13.5 |
| Example 28 | Methanol: 50 | Compound 1-25: 1 | 76.5 | 80.8 | 85.4 | 13.0 |

TABLE 3-continued

| Example | Alcohol content (ppm) | The first additive and its content (%) | Capacity retention rate (%) after 1000 cycles under 45° C. at 1 C | Storage at 60° C. for 30 days Capacity retention rate (%) | Capacity recovery rate (%) | Volume expansion rate (%) |
|---|---|---|---|---|---|---|
| Example 29 | Methanol: 50 | Compound 1-27: 1 | 78.2 | 81.0 | 85.3 | 11.8 |
| Example 30 | Methanol: 50 | Compound 1-30: 1 | 78.8 | 80.4 | 86.1 | 11.9 |
| Example 31 | Methanol: 50 | Compound 1-31: 1 | 78.1 | 81.1 | 86.2 | 11.9 |
| Example 32 | Methanol: 50 | Compound 1-33: 1 | 75.7 | 78.5 | 81.2 | 16.3 |
| Example 33 | Methanol: 50 | Compound 1-36: 1 | 72.8 | 76.5 | 80.0 | 17.0 |
| Example 34 | Methanol: 50 | Compound 1-37: 1 | 73.3 | 75.3 | 76.0 | 16.9 |
| Example 35 | Methanol: 50 | Compound 1-38: 1 | 74.3 | 76.2 | 79.6 | 18.8 |
| Example 36 | Methanol: 50 | Compound 1-40: 1 | 72.5 | 74.3 | 77.1 | 22.1 |
| Comparative Example 1 | Methanol: 50 | — | 63.4 | 63.3 | 69.9 | 27.3 |

As can be seen from the testing results in Table 3, the compound of formula (I) with a variable structure, when added to the electrolyte being of the methanol content of 200 ppm or less, enhances the cycling and storage performances under the high temperature of the baiter to different extend.

2.1.4 Results from testing the batteries prepared in Examples 37 to 48 and Comparative Examples 1 and 7-9 are shown in Table 4.

TABLE 4

| Example | The first additive and its content (%) | The second additive and its content (%) | Storage at 60° C. for 30 days Capacity retention rate (%) | Volume expansion rate (%) |
|---|---|---|---|---|
| Example 37 | Compound 1-1: 0.05 | Compound 5-2: 4 | 80.7 | 8.9 |
| Example 38 | Compound 1-1: 0.1 | Compound 5-2: 3 | 81.5 | 7.6 |
| Example 39 | Compound 1-1: 0.5 | Compound 5-2: 2 | 82.1 | 5.7 |
| Example 40 | Compound 1-1: 1 | Compound 5-2: 1 | 84.6 | 7.9 |
| Example 41 | Compound 1-1: 2 | Compound 5-2: 0.5 | 83.6 | 3.7 |
| Example 42 | Compound 1-1: 3 | Compound 5-2: 0.1 | 84.0 | 4.8 |
| Example 43 | Compound 1-1: 5 | Compound 5-2: 0.05 | 78.9 | 5.2 |
| Example 44 | Compound 1-5: 1 | Compound 5-1: 1 | 86.4 | 4.1 |
| Example 45 | Compound 1-13: 1 | Compound 5-3: 1 | 85.6 | 3.9 |
| Example 46 | Compound 1-20: 1 | Compound 5-4: 1 | 85.8 | 4.4 |
| Example 47 | Compound 1-22: 1 | Compound 6-1: 1 | 86.0 | 3.7 |
| Example 48 | Compound 1-30: 1 | Compound 6-4: 1 | 83.8 | 4.6 |
| Comparative Example 1 | — | — | 63.3 | 27.3 |
| Comparative Example 7 | Compound 1-1: 1 | — | 80.5 | 10.1 |
| Comparative Example 8 | — | Compound 5-2: 1 | 73.7 | 25.2 |
| Comparative Example 9 | — | Compound 6-1: 1 | 71.8 | 24.6 |

As can be seen from the testing results in Table 4, as compared to the first additive or the second additive added alone, the first additive and the second additive added in combination to the non-aqueous electrolyte effectively increases the capacity retention rate of the lithium-ion battery after storage under the high temperature and remarkably suppresses gas generation of the lithium battery, thus maintaining volume stability of the lithium-ion battery under high temperature, avoiding the lithium-ion battery from expanding and bulging. Besides, as shown in Table 4, the first additive and the second additive, added in combination respectively at an amount of 0.5% to 2% exhibit the optimal synergistically improved storage performance under the high temperature.

2.2. The lithium batteries prepared in Examples 49 to 59 and Comparative Examples 10 to 16 were tested for the following performances.

Testing on the Cycling Performance Under the High Temperature

In an oven at a constant temperature of 45° C., the lithium-ion battery prepared ($LiNi_{0.5}Co_{0.2}Mn_{0.3}O_2$/AG) was charged at a constant current of 1 C to achieve 4.4 V; then subjected to constant current and constant voltage charging until the current drops to 0.05 C; and then discharged at a constant current of 1 C back to 3.0 V, so as to circulate in this way, and the first discharge capacity and the last discharge capacity were recorded.

The impedance increasing rate for high temperature cycle was calculated according to the following equation:

$$\text{Impedance increasing rate} = (\text{impedance after the last discharging} - \text{impedance after the first discharging})/\text{impedance after the first discharging} \times 100\%$$

After 1000 cycles under the high temperature, the battery was disassembled to obtain the negative electrode plate, the passive film at the surface of which was analyzed for the proportion of the inorganic component. The passive film at the negative electrode plate was tested and analyzed for respective proportions by X-ray photoelectron spectroscopy (XPS). In specific, after washing the electrolyte remained on the surface with DMC, and transferred by a vacuum transfer chamber to the PHI versaprobe III instrument, the negative electrode plate was tested for components on the surface, with spectral peaks filled using the multipack software at the end of the testing.

Results from testing the batteries prepared in Examples 49 to 59 and Comparative Examples 10 to 16 are shown in Table 5.

TABLE 5

| Example | The first additive and its content (%) | The third additive and its content (%) | 1000 cycles under 45° C. at 1 C<br>Impedance increasing rate (%) | 1000 cycles under 45° C. at 1 C<br>Proportion of the inorganic component in the passive film (%) |
|---|---|---|---|---|
| Example 49 | Compound 1-1: 0.05 | LiODFB: 3 | 60.7 | 89.2 |
| Example 50 | Compound 1-1: 0.1 | LiODFB: 2 | 48.1 | 80.8 |
| Example 51 | Compound 1-1: 0.5 | LiODFB: 1 | 42.3 | 70.7 |
| Example 52 | Compound 1-1: 1 | LiODFB: 0.8 | 35.5 | 60.5 |
| Example 53 | Compound 1-1: 2 | LiODFB: 0.5 | 27.4 | 45.5 |
| Example 54 | Compound 1-1: 3 | LiODFB: 0.1 | 22.4 | 32.3 |
| Example 55 | Compound 1-1: 5 | LiODFB: 0.05 | 18.9 | 25.7 |
| Example 56 | Compound 1-5: 1 | $LiPO_2F_2$: 0.8 | 38.0 | 62.7 |
| Example 57 | Compound 1-13: 1 | LiDFOP: 0.8 | 38.9 | 58.9 |
| Example 58 | Compound 1-20: 1 | $LiBF_4$: 0.8 | 37.7 | 59.0 |
| Example 59 | Compound 1-28: 1 | LiBOB: 0.8 | 36.9 | 57.0 |
| Comparative Example 10 | — | — | 75.7 | 31.2 |
| Comparative | Compound 1-1: 1 | — | 39.9 | 24.1 |

What is claimed is:

1. A non-aqueous electrolyte, comprising a solvent, an electrolytic salt, a first additive, and a third additive, wherein the first additive is one or more selected from a compound of formula (I):

$$A-D-B-E-C, \text{ wherein:} \quad (I)$$

A, B and C each are independently selected from a group containing a cyclic carbonate group, a cyclic sulfate group, a cyclic sulfite group, a cyclic sulfonate group, a cyclic sulfone group, a cyclic sulfoxide group, a cyclic carboxylate group or a cyclic anhydride group; and D and E each are independently selected from a single bond, or a group containing hydrocarbylene group, an ether bond, a sulfur-oxygen double bond, or a carbon-oxygen double bond, wherein the first additive is added at an amount of 0.01% to 5.0% based on a total mass of 100% of the non-aqueous electrolyte, wherein the third additive is one or more selected from $LiPO_2F_2$, LiODFB, LiDFOP, LiBOB, $LiBF_4$, LiFSI or LiTFSI, wherein the third additive is added at an amount of 0.01% to 4% based on the total mass of 100% of the non-aqueous electrolyte, and wherein the non-aqueous electrolyte is of a methanol content of 200 ppm or less, wherein the first additive is one or more selected from the following compounds Compound 1-1

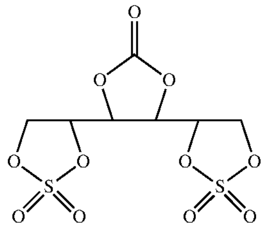

Compound 1-2

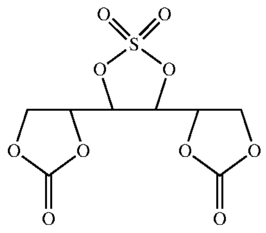

Compound 1-3

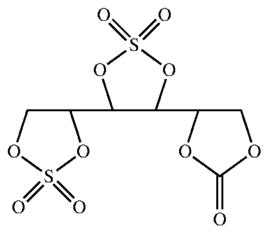

-continued

Compound 1-4

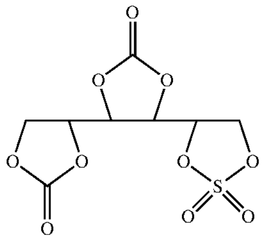

Compound 1-5

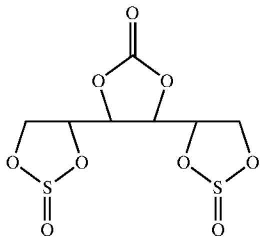

Compound 1-6

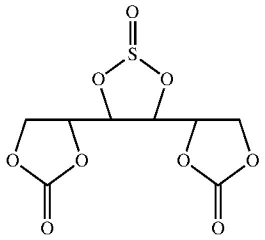

Compound 1-7

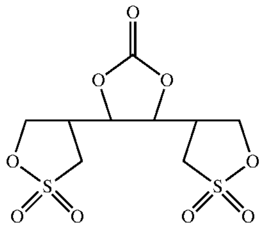

Compound 1-8

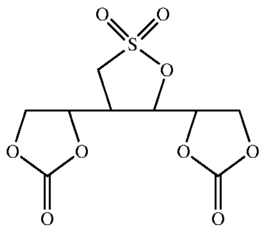

Compound 1-9

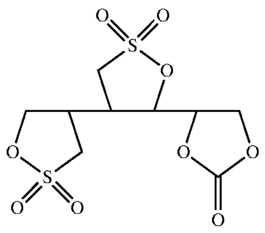

-continued
Compound 1-10
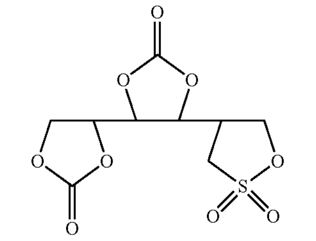
Compound 1-11
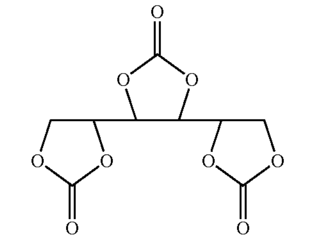
Compound 1-12
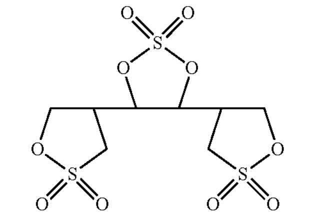
Compound 1-13
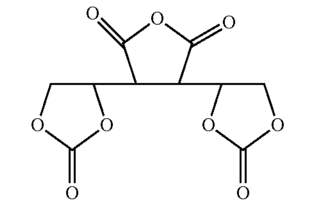
Compound 1-14
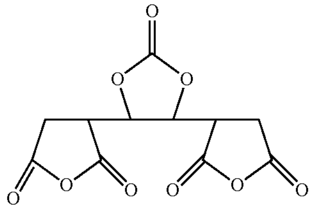
Compound 1-15
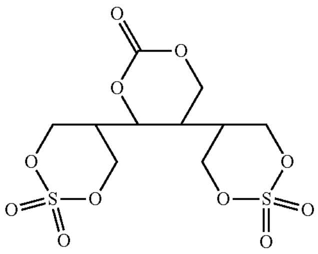
-continued
Compound 1-16
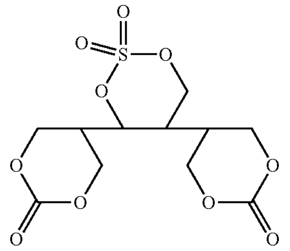
Compound 1-17
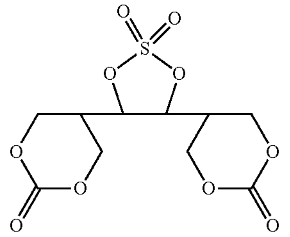
Compound 1-18
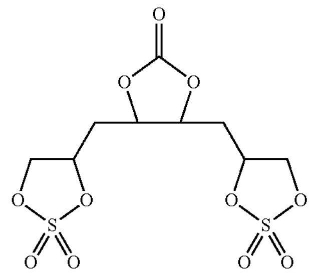
Compound 1-19
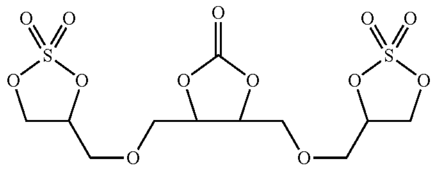
Compound 1-20
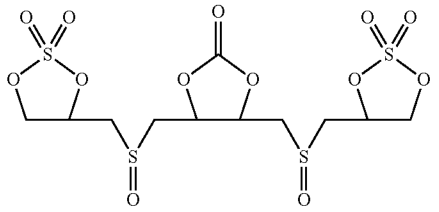
Compound 1-21
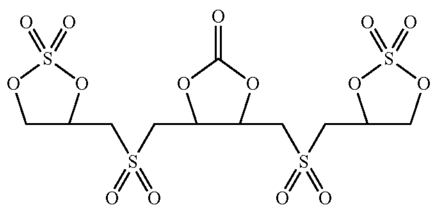

-continued
Compound 1-22
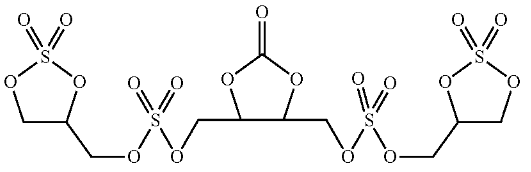
Compound 1-23
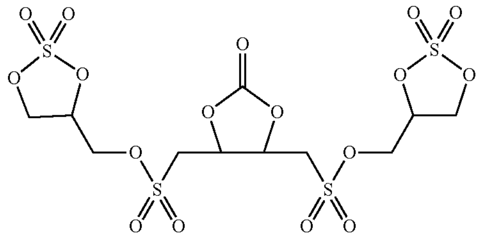
Compound 1-24
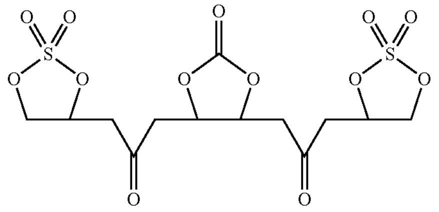
Compound 1-25
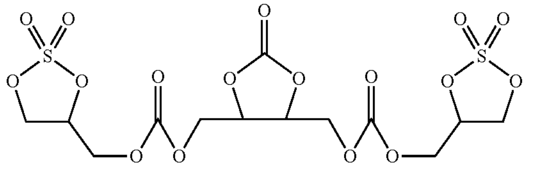
Compound 1-26
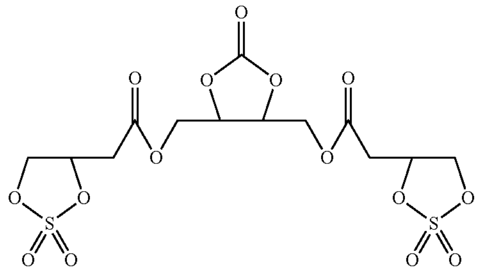
Compound 1-27
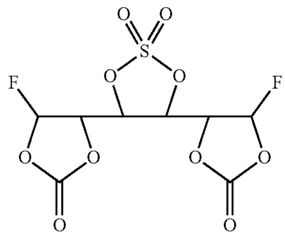
-continued
Compound 1-28
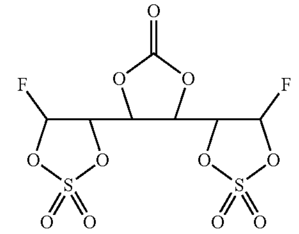
Compound 1-29
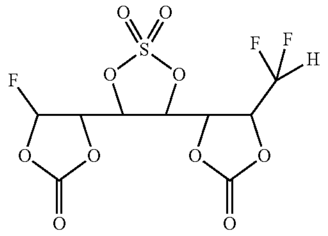
Compound 1-30
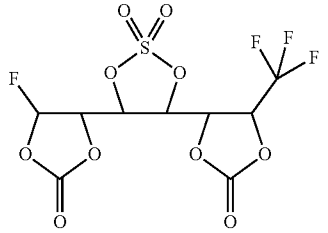
Compound 1-31
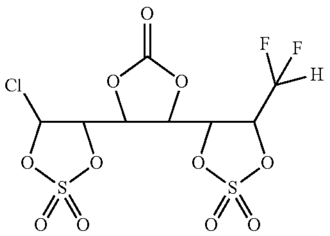
Compound 1-32
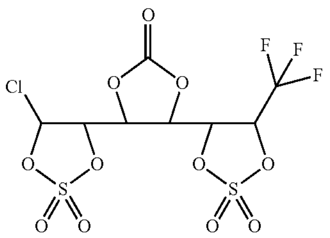
Compound 1-33
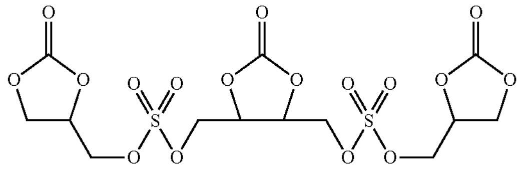

-continued

Compound 1-34

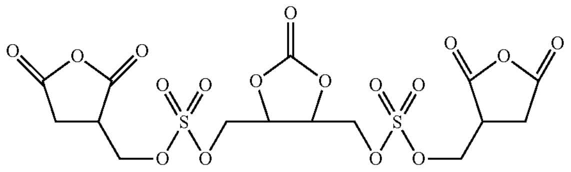

Compound 1-35

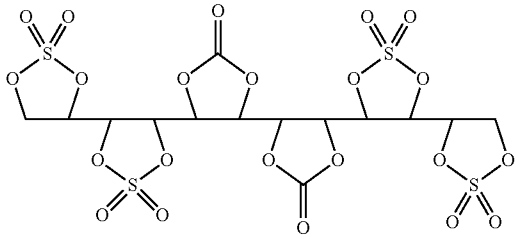

Compound 1-36

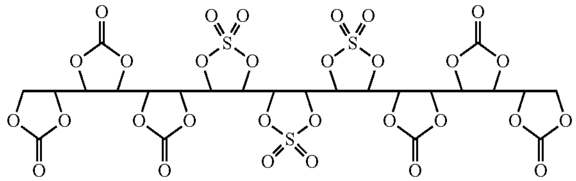

Compound 1-37

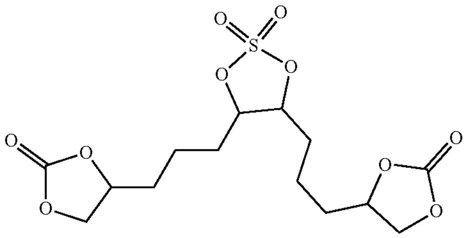

Compound 1-38

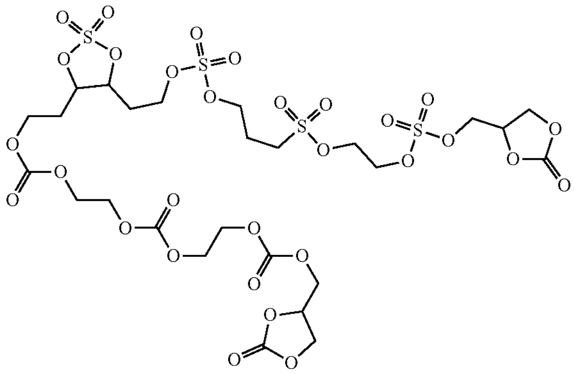

Compound 1-39

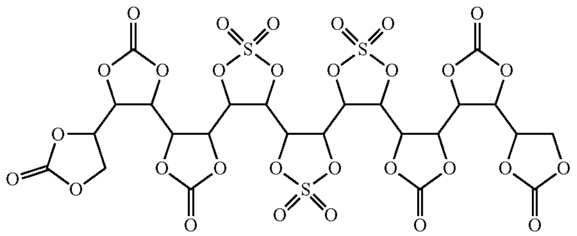

-continued

Compound 1-40

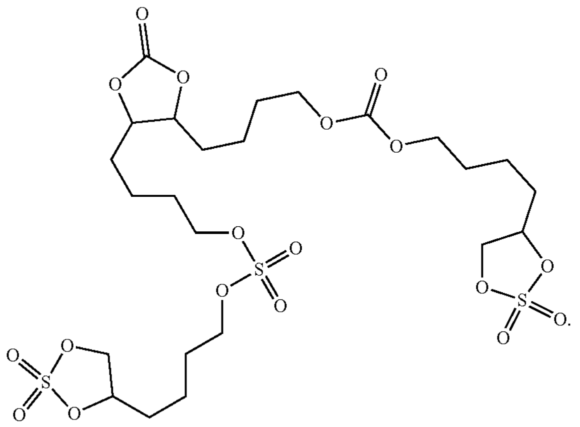

2. The non-aqueous electrolyte according to claim 1, wherein:

A, B and C each independently contain 1 to 5 of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group(s) and the cyclic anhydride group(s); and a total number of the cyclic carbonate group(s), the cyclic sulfate group(s), the cyclic sulfite group(s), the cyclic sulfonate group(s), the cyclic sulfone group(s), the cyclic sulfoxide group(s), the cyclic carboxylate group(s) and the cyclic anhydride group(s) contained in A, B and C is less than or equal to 10.

3. The non-aqueous electrolyte according to claim 1, wherein A and C each are independently selected from a group of formula (II):

(II)

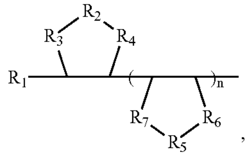

wherein n is an integer selected from 0 to 4;

$R_1$ is selected from hydrogen, halogen, a $C_1$-$C_5$ hydrocarbyl group or a $C_1$-$C_5$ halogenated hydrocarbyl group, $R_2$, $R_3$, $R_4$, $R_5$, $R_6$ and $R_7$ each are independently selected from a $C_1$-$C_3$ hydrocarbylene group, a $C_1$-$C_3$ alkoxy group, an oxygen atom,

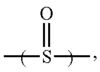, 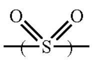 or 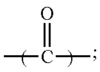;

at least one among $R_2$, $R_3$ and $R_4$ is selected from

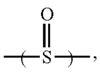, 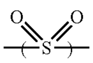 or 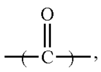, and at least one among $R_2$, $R_3$ and $R_4$ is the oxygen atom; and at least one among $R_5$, $R_6$, and $R_7$ is selected from

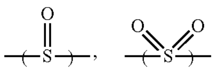 or 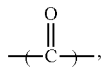

and at least one among $R_5$, $R_6$, and $R_7$ is the oxygen atom.

4. The non-aqueous electrolyte according to claim 1, wherein B is selected from a group of formula (III):

(III)

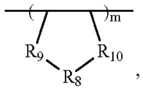

wherein m is an integer selected from 1 to 4;

$R_8$, $R_9$ and $R_{10}$ each are independently selected from a $C_1$-$C_3$ hydrocarbylene group, a $C_1$-$C_3$ alkoxy group, an oxygen atom,

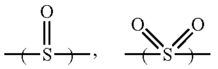 or 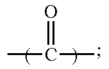;

and at least one among $R_8$, $R_9$ and $R_{10}$ is selected from

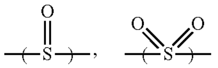 or 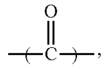

and at least one among $R_8$, $R_9$ and $R_{10}$ is the oxygen atom.

5. The non-aqueous electrolyte according to claim 1, wherein D and E each are independently selected from a group of formula (IV):

(IV)

$$-(R_{11}-R_{12}-R_{13})_z-,$$

wherein z is an integer selected from 0 to 4;

$R_{11}$ and $R_{13}$ each are independently selected from a single bond or a $C_1$-$C_5$ hydrocarbylene group; and $R_{12}$ is selected from a single bond,

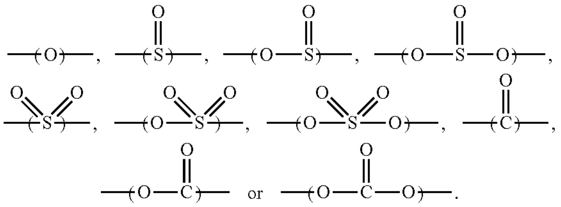

or

6. The non-aqueous electrolyte according to claim 1, wherein D and E each are independently selected from a single bond or a $C_1$-$C_5$ hydrocarbylene group; and A, B and C each are independently selected from a substituted or unsubstituted cyclic carbonate group, a substituted or unsubstituted cyclic sulfate group, a substituted or unsubstituted cyclic sulfite group, a substituted or unsubstituted cyclic sulfonate group, a substituted or unsubstituted cyclic sulfone group, a substituted or unsubstituted cyclic sulfoxide group, a substituted or unsubstituted cyclic carboxylate group, or a substituted or unsubstituted cyclic anhydride group.

7. The non-aqueous electrolyte according to claim 1, wherein:

A and C are same to each other;

A and B are same or different to each other; and

D and E are same to each other.

8. The non-aqueous electrolyte according to claim 1, further comprising a second additive, wherein the second additive is one or more selected from a compound of formula (V) or a compound of formula (VI); and the second additive is added at an amount of 0.01% to 4% based on the total mass of 100% of the non-aqueous electrolyte, (V)

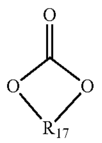

(VI)

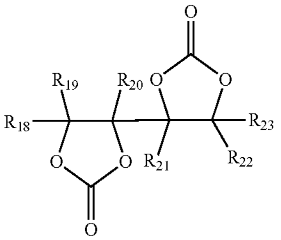

wherein $R_{17}$ is selected from a $C_2$-$C_5$ fluoro-hydrocarbylene group or a $C_2$-$C_5$ unsaturated hydrocarbylene group; and $R_{18}$, $R_{19}$, $R_{20}$, $R_{21}$, $R_{22}$ and $R_{23}$ each are independently selected from a hydrogen atom, a halogen atom, a $C_1$-$C_5$ saturated or unsaturated hydrocarbyl group or a $C_1$-$C_5$ halogenated hydrocarbyl group.

9. The non-aqueous electrolyte according to claim 8, wherein:

the compound of formula (V) is one or more selected from the following compounds:

Compound 5-1

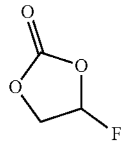

Compound 5-2

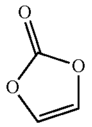

-continued

Compound 5-3

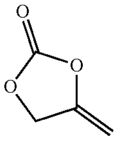

Compound 5-4

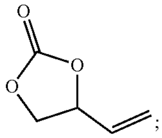;

the compound of formula (VI) is one or more selected from the following compounds:

Compound 6-1

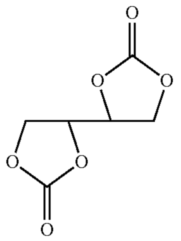

Compound 6-2

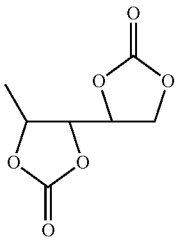

Compound 6-3

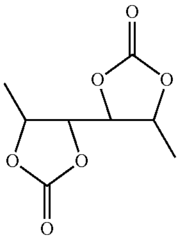

-continued

Compound 6-4

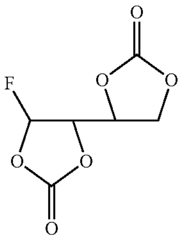

Compound 6-5

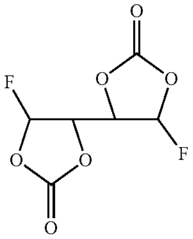

Compound 6-6

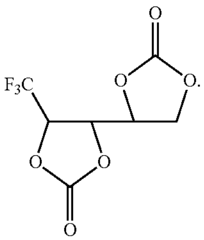

10. A battery, comprising a positive electrode, a negative electrode and a non-aqueous electrolyte according to claim 1.

11. The non-aqueous electrolyte according to claim 6, wherein when A, B or C is substituted, the substitution is selected from halogen, a hydrocarbyl group, or a halogenated hydrocarbyl group.

12. The non-aqueous electrolyte according to claim 11, wherein when A, B or C is substituted, the substitution is selected from halogen, an alkyl group or a halogenated alkyl group.

* * * * *